United States Patent [19]

Dubief et al.

[11] Patent Number: 6,022,836
[45] Date of Patent: *Feb. 8, 2000

[54] DETERGENT COSMETIC COMPOSITIONS AND THEIR USE

[75] Inventors: Claude Dubief, Le Chesnay; Danièle Cauwet-Martin, Paris, both of France

[73] Assignee: L'Oréal, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/675,827

[22] Filed: Jun. 5, 1996

[30] Foreign Application Priority Data

Jul. 7, 1995 [FR] France ................................. 9508271

[51] Int. Cl.⁷ ............................... C11D 1/02; C11D 3/02; A61K 7/075
[52] U.S. Cl. ........................ 510/122; 510/466; 510/123; 510/124; 510/126; 510/470; 424/70.12; 424/70.122; 424/70.13; 424/70.14; 424/70.17
[58] Field of Search ................................. 510/122, 123, 510/124, 126, 466, 470; 424/70.12, 70.122, 70.13, 70.14, 70.17

[56] References Cited

U.S. PATENT DOCUMENTS

| | | | |
|---|---|---|---|
| 4,710,314 | 12/1987 | Madrange et al. | 252/117 |
| 4,820,308 | 4/1989 | Madrange | 8/405 |
| 5,077,041 | 12/1991 | Yamashina et al. | 424/70 |
| 5,100,657 | 3/1992 | Ansher-Jackson et al. | 424/70 |
| 5,246,694 | 9/1993 | Birtwistle | 424/70 |
| 5,307,327 | 4/1994 | Birtwistle | 252/547 |
| 5,344,643 | 9/1994 | Thiel et al. | 424/70 |
| 5,362,485 | 11/1994 | Hayama et al. | 424/70 |
| 5,409,628 | 4/1995 | Heinz et al. | 252/124.17 |
| 5,468,477 | 11/1995 | Kumar et al. | 427/78.17 |
| 5,536,493 | 7/1996 | Dubief et al. | 424/70.13 |
| 5,541,276 | 7/1996 | Thimineur et al. | 528/10 |
| 5,650,383 | 7/1997 | Dubief et al. | 510/122 |
| 5,658,557 | 8/1997 | Bolich, Jr. et al. | 424/70.12 |

FOREIGN PATENT DOCUMENTS

| | | |
|---|---|---|
| 0 219 830 | 10/1986 | European Pat. Off. . |
| 0 392 320 | 4/1990 | European Pat. Off. . |
| 0 531 650 | 7/1992 | European Pat. Off. . |
| 0 582 152 | 7/1993 | European Pat. Off. . |
| 0 582 152 A2 | 2/1994 | European Pat. Off. . |
| 93/23009 | 5/1993 | WIPO . |
| 94/06409 | 9/1993 | WIPO . |

*Primary Examiner*—Kery Fries
*Attorney, Agent, or Firm*—Finnegan, Henderson, Farabow, Garrett, & Dunner, LLP

[57] ABSTRACT

A detergent hair composition of the type including, in a cosmetically acceptable medium, a washing base and at least one cationic polymer, and additionally comprising at least one water-soluble or water-dispersible silicone compound including a silicone main chain onto which at least one hydrocarbon group of anionic nature is grafted.

This composition may be applied to clean, care and style hair and gives an improved styling effect.

42 Claims, No Drawings

DETERGENT COSMETIC COMPOSITIONS AND THEIR USE

The present invention relates to new cosmetic compositions with improved properties, intended simultaneously for the cleaning, conditioning and styling of hair and including, in a cosmetically acceptable support, a washing base comprising surfactants with detergent power, in which conditioning agents of cationic polymer type are also present in combination with particular silicone derivatives (silicone compounds). The invention also relates to the use of the said compositions in the abovementioned cosmetic application.

The use of detergent hair compositions (or shampoos) based essentially on conventional surface-active agents especially of anionic, nonionic and/or amphoteric type, but more particularly of anionic type is commonplace for cleaning and/or washing hair. These compositions are applied to wet hair, and the foam generated by massaging or rubbing with the hands permits, after rinsing with water, the removal of the diverse soiling previously present on the hair.

These base compositions undoubtedly have good washing power, but the intrinsic cosmetic properties attached to them nevertheless remain fairly weak, especially because of the fact that the relatively aggressive nature of such a cleaning treatment can in the long term inflict more or less marked damage on the hair fibre, this being related in particular to the gradual removal of the lipids or proteins present in or at the surface of the latter.

Also, in order to improve the cosmetic properties of the above detergent compositions, and more particularly of those which are called upon to be applied to sensitized hair (i.e. hair which is found to be damaged or embrittled especially by the chemical action of atmospheric agents and/or of hair treatments such as permanent waving, dyeing or bleaching), it is now usual to introduce into the latter complementary cosmetic agents known as conditioning agents, intended chiefly to repair or limit the detrimental or undesirable effects induced by the various treatments or attacks to which the hair fibres are more or less repeatedly subjected. These conditioning agents can, of course, also improve the cosmetic behaviour of natural hair.

The conditioning agents most commonly employed nowadays in shampoos are cationic polymers, which, in fact, endow washed, dry or wet hair with an ease of disentangling, a smoothness and a sleekness which are markedly enhanced in relation to what can be obtained with the corresponding cleaning compositions which do not contain cationic polymers.

Furthermore, for some time, attempts have been made to obtain conditioning shampoos which are capable of imparting to the washed hair not only the cosmetic properties referred to above, but also, to a more or less advanced degree, styling, body, hair shaping and style holding properties. These latest washing shampoos with improved general cosmetic properties are often called, for simplicity, "shampoos with styling effects" an expression which will, furthermore, be referred to again in the description which follows.

However, and despite the progress made recently in the field of shampoos with styling effects based on cationic polymers, the latter are not really completely satisfactory, with the result that a requirement still exists at present for new products which exhibit better performance in respect of one or more of the cosmetic properties referred to above.

The present invention is aimed at satisfying such a need.

Thus, following considerable research carried out on the question, it has now been found by the inventors, completely unexpectedly and surprisingly, that by introducing particular and suitably selected silicone derivatives, as defined below, into detergent hair compositions containing cationic polymers as conditioning agents, it is possible to improve substantially and significantly the cosmetic properties attached to the latter, and to do so while maintaining their good intrinsic washing power.

Without wishing to limit the present invention to some theory or other, it would appear that interactions and/or particular affinities exist between the cationic polymers, the silicone derivatives in accordance with the invention, and hair, which promote a uniform, considerable and durable deposition of the silicone derivatives at the surface of the hair, this qualitative and quantitative deposition being probably one of the causes of the improvement observed in the final cosmetic properties, in particular the ease of styling, the style holding, the liveliness and the body of the treated hair.

In any event, the cosmetic properties attached to the washing bases containing the combination of agents (cationic polymer/specific silicone derivative) in accordance with the invention are markedly superior to those that can be obtained by using only one of these agents at equivalent overall concentration.

The present invention is based on all these discoveries.

Thus, according to the present invention, new detergent hair compositions are now proposed, of the type including, in a cosmetically acceptable medium, a washing base and at least one cationic polymer, and which are essentially characterized in that they additionally comprise at least one water-soluble or water-dispersible silicone derivative including a silicone main chain onto which at least one hydrocarbon group of anionic nature is grafted.

Another objective of the invention is the use of the above compositions in cosmetics for the cleaning, conditioning and styling of hair.

However, other characteristics, aspects and advantages of the invention will appear still more clearly on reading the description which is to follow and the concrete examples intended to illustrate it, without any limitation being implied.

As indicated above, the preferred constituents which enter into the composition of the hair products of the invention are:
(i) the surfactant(s) with detergent power intended to form the washing base;
(ii) the conditioning agent(s) of cationic polymer type; and
(iii) the specific water-soluble or water-dispersible silicone derivative(s).

A- WASHING BASE

The compositions in accordance with the invention necessarily include a washing base, generally aqueous.

The surfactant(s) forming the washing base may be equally well chosen, by themselves or as mixtures, from anionic, amphoteric, nonionic, zwitterionic and cationic surfactants.

The minimum quantity of washing base is that just sufficing to endow the final composition with a satisfactory foamability and/or detergency, and excessive quantities of washing base do not really bring any additional advantages.

Thus, according to the invention, the washing base may preferably represent from 4% to 30% by weight, more preferably from 10% to 25% by weight, and still more preferably from 12% to 20% by weight, of the total weight of the final composition.

The surfactants which are suitable for making use of the present invention are especially the following:

(i) Anionic surfactant(s):

Their nature does not assume a really critical character within the context of the present invention.

Thus, by way of example of anionic surfactants that can be employed, by themselves or as mixtures, in the context of the present invention, there may be mentioned especially (nonlimiting list) the salts (in particular alkali metal, especially sodium, salts, ammonium salts, amine salts, aminoalcohol salts or magnesium salts) of the following compounds: alkyl sulphates, alkyl ether sulphates, alkylamido ether sulphates, alkylarylpolyether sulphates, monoglyceride sulphates, alkylsulphonates, alkyl phosphates, alkylamidesulphonates, alkylarylsulphonates, α-olefinsulphonates, paraffinsulphonates, alkylsulphosuccinates, alkyl ether sulphosuccinates, alkylamidesulphosuccinates, alkylsulphosuccinamates, alkylsulphoacetates, alkyl ether phosphates, acylsarcosinates, acylisethionates and N-acyltaurates, the alkyl or acyl radical of all these different compounds preferably containing from 12 to 20 carbon atoms, and the aryl radical preferably denoting a phenyl or benzyl group.

Among the anionic surfactants which are further usable there may also be mentioned the salts of fatty acids such as the salts of oleic, ricinoleic, palmitic and stearic acids, the acids of copra oil or of hydrogenated copra oil, and acyllactylates in which the acyl radical contains from 8 to 20 carbon atoms.

It is also possible to employ weakly anionic surfactants, like alkyl-D-galactosideuronic acids and salts thereof, as well as the polyoxyalkylenated carboxylic ether acids and their salts, in particular those containing from 2 to 50 ethylene oxide groups and mixtures thereof. The anionic surfactants of the polyalkoxyalkylenated carboxylic ether acid or salt type are in particular those which correspond to the following formula (1):

$$R_1-(OC_2H_4)_n-OCH_2COOA \qquad (1)$$

wherein:

$R_1$ denotes an alkyl or alkaryl group, the alkyl radical preferably containing from 6 to 20 carbon atoms, and aryl preferably denoting phenyl;

n is a whole or decimal number (mean value) which can preferably range from 2 to 24 and more preferably from 3 to 10; and A denotes H, ammonium, Na, K, Li, Mg or a monoethanolamine or triethanolamine residue.

It is also possible to employ mixtures of compounds of formula (1), in particular mixtures in which the groups $R_1$ are different.

Compounds of formula (1) are sold, for example, by the Chem Y company under the names Akypos (NP40, NP70, OP40, OP80, RLM25, RLM38, RLMQ 38 NV, RLM 45, RLM 45 NV, RLM 100, RLM 100 NV, RO 20, RO 90, RCS 60, RS 60, RS 100 and RO 50) or by the Sandoz company under the names Sandopan (DTC Acid, DTC).

(ii) Nonionic surfactant(s):

The nonionic surface-active agents themselves are also compounds which are well known per se (in this respect see especially the "Handbook of Surfactants" by M. R. Porter, published by Blackie & Son (Glasgow and London), 1991, pp. 116–178, the disclosure of which is specifically incorporated by reference herein) and, in the context of the present invention, their nature does not assume any critical character.

They can thus be selected especially from (nonlimiting list) alcohols, alpha-diols, alkylphenols and polyethoxylated, polypropoxylated and polyglycerolated fatty acids which have a fatty chain containing, for example, 8 to 18 carbon atoms, it being possible for the number of ethylene oxide or propylene oxide groups to preferably range from 2 to 50 and it being possible for the number of glycerol groups to preferably range from 2 to 30.

The copolymers of ethylene oxide and propylene and the condensates of ethylene oxide and propylene with fatty alcohols may also be mentioned; the polyethoxylated fatty amides preferably containing from 2 to 30 moles of ethylene oxide, the polyglycerolated fatty amides on average containing 1 to 5 glycerol groups and in particular 1.5 to 4, the polyethoxylated fatty amines preferably containing 2 to 30 moles of ethylene oxide, the oxyethylenated esters of sorbitan fatty acids containing from 2 to 30 moles of ethylene oxide, the sucrose esters of fatty acids, the polyethylene glycol esters of fatty acids, alkylpolyglycosides, the N-alkylglucamine derivatives, amine oxides such as the oxides of $C_{10}$–$C_{14}$-alkylamines or the N-acylaminopropylmorpholine oxides. It will be noted that alkylpolyglycosides constitute nonionic surfactants which enter particularly well into the scope of the present invention.

(iii) Amphoteric or zwitterionic surfactant(s):

The amphoteric or zwitterionic surface-active agents, the nature of which does not assume any critical character in the context of the present invention, may preferably be (nonlimiting list) derivatives of aliphatic secondary or tertiary amines in which the aliphatic radical is a linear or branched chain containing 8 to 18 carbon atoms and containing at least one water-solubilizing anionic group (for example carboxylate, sulphonate, sulphate, phosphate or phosphonate); alkyl($C_8$–$C_{20}$)betaines, sulphobetaines, alkyl ($C_8$–$C_{20}$)amidoalkyl($C_1$–$C_6$)betaines or alkyl($C_8$–$C_{20}$) amidoalkyl($C_1$–$C_6$)sulphobetaines may further be mentioned.

Among the amine derivatives there may be mentioned products sold under the name Miranol, as described in patents U.S. Pat. No. 2,528,378 and U.S. Pat. No. 2,781,354 and classified in the CTFA dictionary, 3rd edition, 1982, the disclosures of which are specifically incorporated by reference herein, under the names Amphocarboxyglycinates and Amphocarboxypropionates, of respective structures:

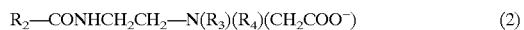

$$R_2-CONHCH_2CH_2-N(R_3)(R_4)(CH_2COO^-) \qquad (2)$$

wherein $R_2$ denotes an alkyl radical of an acid $R_2$—COOH present in hydrolysed copra oil, a heptyl, nonyl or undecyl radical, $R_3$ denotes a beta-hydroxyethyl group and $R_4$ a carboxymethyl group; and

$$R_2'-CONHCH_2CH_2-N(B)(C) \qquad (3)$$

wherein:

B denotes —$CH_2CH_2OX'$, C denotes —$(CH_2)_z$—Y', with z=1 or 2,

X' denotes the —$CH_2CH_2$—COOH group or a hydrogen atom

Y' denotes —COOH or the radical —$CH_2$—CHOH—$SO_3H$ $R_2'$ denotes an alkyl radical of an acid $R_9$—COOH present in copra oil or in hydrolysed linseed oil, wherein $R_9$ is an alkyl radical, especially $C_7$, $C_9$, $C_{11}$ or $C_{13}$, a $C_{17}$ alkyl radical and its iso form or an unsaturated radical $C_{17}$.

By way of example there may be mentioned the cocoamphocarboxyglycinate sold under the trade name Miranol C2M concentrated by the Miranol company.

(iv) Cationic surfactants:

Among the cationic surfactants there may be mentioned in particular (nonlimiting list): the salts of optionally polyoxyalkylenated primary, secondary or tertiary fatty amines, quaternary ammonium salts such as tetraalkylammonium, alkylamidoalkyltrialkylammonium, trialkylbenzylammonium, trialkylhydroxyalkylammonium or alkylpyridinium chlorides or bromides, imidazoline derivatives, or amine oxides of cationic nature.

It will be noted that the cationic surfactants, the use of which is not ruled out, do not constitute the preferred surfactants for making use of the present invention.

B- CATIONIC POLYMER(S)

The compositions in accordance with the invention additionally necessarily include a cationic polymer.

The conditioning agents of cationic polymer type which can be employed in accordance with the present invention may be selected from all those already known per se as improving the cosmetic properties of hair treated with detergent compositions, namely especially those described in patent application EP-A-0 337,354 and in French patent applications FR-A-2,270,846, 2,383,660, 2,598,611, 2,470, 596 and 2,519,863, the disclosures of which are specifically incorporated herein.

Still more generally, within the meaning of the present invention, the expression "cationic polymer" denotes any polymer containing cationic groups or groups that can ionize to cationic groups.

The preferred cationic polymers are chosen from those which contain units comprising primary, secondary, tertiary and/or quaternary amine groups which may either form part of the main polymer chain or be carried by a side substituent bonded directly to the latter.

The cationic polymers employed have generally a molecular mass preferably ranging from 500 to $5 \times 10^3$ and more preferably from $10^3$ to $3 \times 10^6$.

Among the cationic polymers, there may be mentioned more particularly quaternized proteins (or protein hydrolysates), quaternized polysiloxanes and polymers of the quaternary polyamine, polyaminoamide and polyammonium type. These are known products.

The quaternized proteins or protein hydrolysates are in particular chemically modified polypeptides carrying quaternary ammonium groups at the end of a chain or grafted onto the latter. Their molecular mass may vary, for example, from 1500 to 10,000, and in particular from 2000 to 5000. Among these compounds there may be mentioned in particular:

the collagen hydrolysates carrying triethylammonium groups, such as the products sold under the name "Quat-Pro E" by the Maybrook company and called "Triethonium Hydrolyzed Collagen Ethosulfate" in the CTFA dictionary;

the collagen hydrolysates carrying trimethylammonium and trimethylstearylammonium chloride groups, sold under the name of "Quat-Pro S" by the Maybrook company and called "Steartrimonium Hydrolyzed Collagen" in the CTFA dictionary;

the animal protein hydrolysates carrying trimethylbenzylammonium groups, such as the products sold under the name "Crotein BTA" by the Croda company and called "Benzyltrimonium hydrolyzed animal protein" in the CTFA dictionary;

the protein hydrolysates carrying, on the polypeptide chain, quaternary ammonium groups comprising at least one alkyl radical containing from 1 to 18 carbon atoms.

Among these protein hydrolysates there may be mentioned, is among others:

"Croquat L" in which the quaternary ammonium groups comprise a $C_{12}$ alkyl group;

"Croquat M" in which the quaternary ammonium groups comprise $C_{10}$–$C_{18}$ alkyl groups;

"Croquat S" in which the quaternary ammonium groups comprise a $C_{18}$ alkyl group;

"Crotein Q" in which the quaternary ammonium groups comprise at least one alkyl group containing from 1 to 18 carbon atoms.

These various products are sold by the Croda company.

Other quaternized proteins or hydrolysates are, for example, those corresponding to the formula:

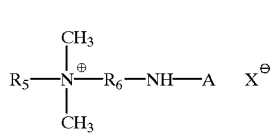

(I)

wherein

X⁻ is an anion of an organic or inorganic acid;

A denotes a protein residue derived from collagen protein hydrolysates;

$R_5$ denotes a lipophilic group containing up to 30 carbon atoms; and $R_6$ denotes an alkylene group containing 1 to 6 carbon atoms.

For example, the products sold by the Inolex company under the name "Lexein QX 3000", called "Cocotrimonium Collagent Hydrolysate" in the CTFA dictionary may be mentioned.

It is further possible to mention quaternized vegetable proteins such as wheat, maize or soya proteins; as quaternized wheat proteins there may be mentioned those marketed by the Croda company under the names "Hydrotriticum WQ or QM", called "Cocodimonium Hydrolysed wheat protein" in the CTFA dictionary, "Hydrotriticum QL" called "Laurdimonium hydrolysed wheat protein" in the CTFA dictionary, or else "Hydrotriticum QS", called "Steardimonium hydrolysed wheat protein" in the CTFA dictionary.

Another class of cationic polymers is that of the silicone cationic polymers. Among these polymers there may be mentioned:

(a) the quaternized polysiloxanes called "amodimethicone" in the CTFA dictionary, and corresponding to the formula:

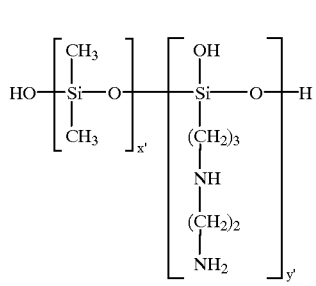

(II)

wherein:

x' and y' are integers depending on the molecular weight, generally such that the molecular weight ranges from 5000 to 10,000;

(b) the silicone cationic polymers corresponding to the formula:

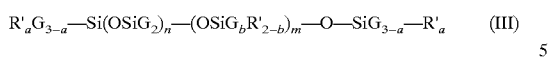   (III)

wherein:

G is a hydrogen atom or a phenyl, OH or $C_1$–$C_8$ alkyl, for example methyl, group;

a denotes the number 0 or an integer from 1 to 3, preferably 0;

b denotes 0 or 1, preferably 1; and m and n are numbers such that the sum (n+m) may vary especially from 1 to 2000 and in particular from 50 to 150, it being possible for n to denote a number from 0 to 1999 and preferably from 49 to 149 and it being possible for m to denote a number from 1 to 2000 and preferably from 1 to 10.

R' is a monovalent radical of formula —$C_qH_{2q}L$ in which q is a number from 2 to 8 and L is an optionally quaternized amine group chosen from the groups:

—NR"—CH$_2$—CH$_2$—N'(R")$_2$

—N(R")$_2$

—N(R")—CH$_2$—CH$_2$—N$^{\oplus R''H}{}_2$A$^-$, wherein:

R" may denote hydrogen, phenyl, benzyl or a monovalent saturated hydrocarbon radical, for example an alkyl radical containing from 1 to 20 carbon atoms; and A$^-$ denotes a halide ion such as, for example, fluoride, chloride, bromide or iodide.

A product corresponding to this definition is the polymer called "trimethylsilylamodimethicone", corresponding to the formula:

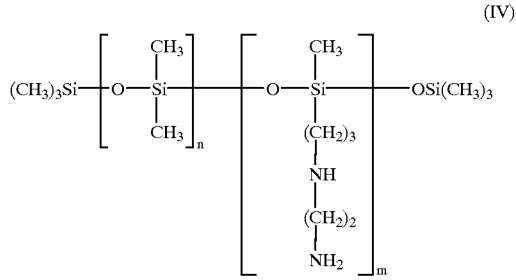   (IV)

wherein:

n and m have the meanings given above in formula III.

Such polymers are described, for example, in patent application EP-A-95238, the disclosure of which is specifically incorporated by reference herein.

(c) the silicone cationic polymers corresponding to the formula:

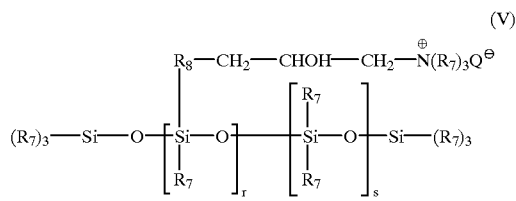   (V)

wherein:

$R_7$ denotes a monovalent hydrocarbon radical containing from 1 to 18 carbon atoms and in particular a $C_1$–$C_{18}$ alkyl or $C_2$–$C_{18}$ alkenyl radical, for example methyl;

$R_8$ denotes a divalent hydrocarbon radical, especially a $C_1$–$C_{18}$ alkylene radical or a divalent $C_1$–$C_{18}$, for example $C_1$–$C_8$, alkyleneoxy radical;

Q$^-$ is a halide ion, especially chloride;

r denotes a mean statistical value from 2 to 20, preferably from 2 to 8; and s denotes a mean statistical value from 20 to 200, preferably from 20 to 50.

Such polymers are described more particularly in U.S. Pat. No. 4,185,087, the disclosure of which is specifically incorporated by reference herein.

A polymer which enters within this class is the polymer sold by the Union Carbide company under the name "Ucar Silicone ALE 563".

When these silicone polymers are used, a particularly advantageous embodiment is their joint use with cationic and/or nonionic surface agents. It is possible, for example, to employ the product sold under the name "Emulsion Cationique DC 929" by the Dow Corning company which, besides amodimethicone, includes a cationic surface agent including a mixture of products corresponding to the formula:

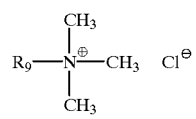

wherein:

$R_9$ denotes alkenyl and/or alkyl radicals containing from 14 to 22 carbon atoms, derived from tallow fatty acids, in combination with a nonionic surface agent of formula:

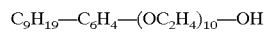

known under the name "Nonoxynol 10".

Another commercial product that can be employed according to the invention is the product sold under the name "Dow Corning Q2 7224" by the Dow Corning company, including, in combination, the trimethylsilylamodimethicone of formula (IV), a nonionic surface agent of formula:

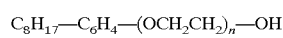

where n=40
also called octoxynol-40,
another nonionic surface agent of formula:

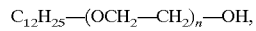

where n=6, also called isolaureth-6, and glycol.

The polymers of the polyamine, polyamidoamide and quaternary polyammonium type, which can be employed in accordance with the present invention, which may be especially mentioned are those described in French patents No. 2,505,348 or 2,542,997, the disclosures of which are specifically incorporated by reference herein. Among these polymers there may be mentioned:

(1) The quaternized or unquaternized dialkylaminoalkyl vinylpyrrolidoneacrylate or -methacrylate copolymers, such as the products sold under the name "Gafquat" by the company GAF Corporation, such as, for example, Gafquat 734, 755 or HS100 or else the product called "Copolymer 937". These polymers are described in detail in French patents 2,077,143 and 2,393,573, the disclosures of which are specifically incorporated by reference herein.

(2) The cellulose ether derivatives comprising quaternary ammonium groups, described in French patent 1,492,597, the disclosure of which is specifically incorporated by reference herein, and in particular the polymers marketed under the names "JR" (JR 400, JR 125, JR 30M) or "LR" (LR 400, LR 30M) by the company Union Carbide Corporation. These polymers are also defined in the CTFA dictionary as hydroxyethyl cellulose quaternary ammoniums which have reacted with an epoxide substituted by a trimethylammonium group.

(3) Cationic cellulose derivatives such as cellulose copolymers or cellulose derivatives grafted with a quaternary ammonium water-soluble monomer, and described especially in U.S. Pat. No. 4,131,576, the disclosure of which is specifically incorporated by reference herein, such as hydroxyalkyl celluloses like hydroxymethyl, hydroxyethyl or hydroxypropyl celluloses grafted especially with a methacryloylethyltrimethylammonium, methacrylamidopropyltrimethylammonium or dimethyidiallylammonium salt.

The commercialized products corresponding to this definition are more particularly the products sold under the name "Celquat L 200" and "Celquat H 100" by the National Starch company.

(4) The cationic polysaccharides described more particularly in U.S. Pat. Nos. 3,589,578 and 4,031,307, the disclosures of which are specifically incorporated by reference herein, and more particularly the product marketed under the name "Jaguar C.13 S" sold by the Meyhall company.

(5) Polymers comprising piperazinyl units and alkylene or hydroxyalkylene divalent radicals with straight or branched chains, optionally interrupted by oxygen, sulphur or nitrogen atoms or by aromatic or heterocyclic rings, as well as the oxidation and/or quaternization products of these polymers. Such polymers are described especially in French patents, 2,162,025 and 2,280,361, the disclosures of which are specifically incorporated by reference herein.

(6) Water-soluble polyaminoamides prepared in particular by polycondensation of an acid compound with a polyamine; these polyaminoamides may be crosslinked with an epihalohydrin, a diepoxide, a dianhydride, an unsaturated dianhydride, a diunsaturated derivative, a bishalohydrin, a bisazetidinium, a bishaloacyidiamine, an alkylbishalide or else with an oligomer resulting from the reaction of a difunctional compound which is reactive towards a bishalohydrin, a bisazetidinium, a bishaloacyidiamine, an alkylbishalide, an epihalohydrin, a diepoxide or a bisunsaturated derivative; the crosslinking agent being employed in proportions ranging from 0.025 to 0.35 moles per amine group of the polyaminoamide; these polyaminoamides may be alkylated or, if they include one or more tertiary amine functional groups, quaternized. Such polymers are described especially in French patents 2,252,840 and 2,368,508, the disclosures of which are specifically incorporated by reference herein.

(7) Polyaminoamide derivatives resulting from the condensation of polyalkylenepolyamines with polycarboxylic acids, followed by an alkylation with difunctional agents. There may be mentioned, for example, the adipic acid—dialkylaminohydroxyalkyldialkylenetriamine polymers in which the alkyl radical contains from 1 to 4 carbon atoms and preferably denotes methyl, ethyl or propyl. Such polymers are described especially in French patent 1,583,363, the disclosure of which is specifically incorporated by reference herein.

Among these derivatives there may be mentioned more particularly the adipic acid/dimethylaminohydroxypropyl/diethylenetriamine polymers sold under the name "Cartaretine F, F4 or F8" by the Sandoz company.

(8) Polymers obtained by reaction of a polyalkylenepolyamine containing two primary amine groups and at least one secondary amine group with a dicarboxylic acid chosen from diglycolic acid and saturated aliphatic dicarboxylic acids preferably containing from 3 to 8 carbon atoms, the molar ratio of the polyalkylenepolyamine to the dicarboxylic acid ranging from 0.8:1 to 1.4:1; the polyaminoamide resulting therefrom being made to react with epichlorohydrin in a molar ratio of epichlorohydrin relative to the secondary amine group of the polyaminoamide ranging from 0.5:1 to 1.8:1. Such polymers are described especially in U.S. Pat. Nos. 3,227,615 and 2,961,347, the disclosures of which are specifically incorporated by reference herein.

Polymers of this type are marketed in particular under the name "Hercosett 57" by the Hercules Inc. company or else under the name of "PD 170" or "Delsette 101" by the Hercules company in the case of the copolymer of adipic acidlepoxypropyl/diethylenetriamine.

(9) Cyclohomopolymers of methyidiallylamine or of dimethyldiallylammonium, such as the homopolymers comprising, as main constituent of the chain, units corresponding to the formulae (VI) or (VI'):

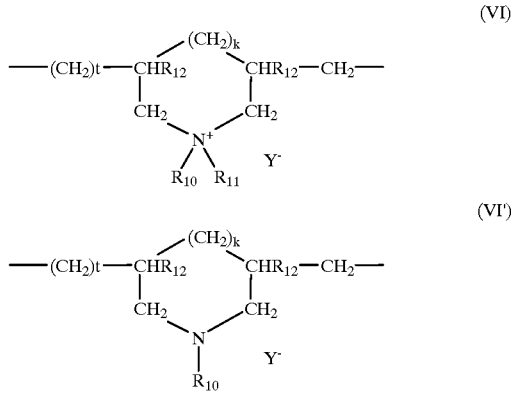

wherein:
formulae k and t are equal to 0 or 1, the sum k+t being equal to 1;
$R_{12}$ denotes a hydrogen atom or a methyl radical;
$R_{10}$ and $R_{11}$ independently denote an alkyl group containing from 1 to 22 carbon atoms, a hydroxyalkyl group in which the alkyl group preferably has 1 to 5 carbon atoms, or a lower amidoalkyl group or
$R_{10}$ and $R_{11}$ may denote, jointly with the nitrogen atom to which they are attached, heterocyclic groups such as piperidinyl or morpholinyl; and Y⁻ is an anion such as bromide, chloride, acetate, borate, citrate, tartrate, bisulphate, bisulphite, sulphate or phosphate.

These polymers are described especially in French patent 2,080,759 and in its certificate of addition 2,190,40, the disclosures of which are specifically incorporated by reference herein.

Among the polymers defined above there may be mentioned more particularly the dimethyldiallylammonium chloride homopolymer sold under the name "Merquat 100" by the Merck company.

(10) The quaternary diammonium polymer containing repeat units corresponding to the formula (VII):

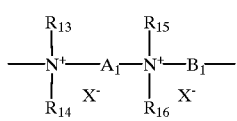 (VII)

wherein $R_{13}$, $R_{14}$, $R_{15}$ and $R_{16}$, independently denote aliphatic, alicyclic or arylaliphatic radicals containing from 1 to 20 carbon atoms or lower hydroxyalkyl aliphatic radicals, or $R_{13}$, $R_{14}$, $R_{15}$ and $R_{16}$, together or separately, form, with the nitrogen atoms to which they are attached, heterocyclic rings optionally containing a second heteroatom other than nitrogen, or $R_{13}$, $R_{14}$, $R_{15}$ and $R_{16}$ denote a linear or branched $C_1$–$C_6$ alkyl radical substituted by a nitrile, ester, acyl, amide or —CO—O—$R_{17}$—D or —CO—NH—$R_{17}$—D group where $R_{17}$ is an alkylene and D a quaternary ammonium group;

$A_1$ and $B_1$ denote polymethylene groups containing from 2 to 20 carbon atoms which may be linear or branched, saturated or unsaturated and which may contain, bonded to or inserted into the main chain, one or several aromatic rings, or one or more oxygen or sulphur atoms or sulphoxide, sulphone, disulphide, amino, alkylamino, hydroxyl, quaternary ammonium, ureido, amide or ester groups, and X⁻ denotes an anion derived from an inorganic or organic acid;

$A_1$, $R_{13}$ and $R_{15}$, with the two nitrogen atoms to which they are attached, may form a piperazine ring;

in addition if $A_1$ denotes a saturated or unsaturated, linear or branched alkylene or hydroxyalkylene radical, $B_1$ may also denote a group $(CH_2)_n$—CO—D—OC—$(CH_2)_n$— in which D denotes:
a) a glycol residue of formula: —O—Z—O—, where Z denotes a linear or branched hydrocarbon radical or a group corresponding to one of the following formulae:

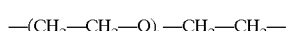

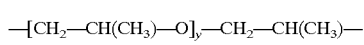

wherein x and y denote an integer from 1 to 4, denoting a defined and unique degree of polymerization or any number from 1 to 4 denoting a mean degree of polymerization;

b) a disecondary diamine residue such as a piperazine derivative;

c) a diprimary diamine residue of formula: —NH—Y—NH—, wherein Y denotes a linear or branched hydrocarbon radical or else the divalent radical

d) a ureylene group of formula: —NH—CO—NH—; and X⁻ is preferably an anion such as chloride or bromide.

These polymers have a molecular mass which generally ranges from 1000 to 100,000.

Polymers of this type are described especially in French patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,495 and 4,027,020, the disclosures of which are specifically incorporated by reference herein.

(11) Quaternary polyammonium polymers comprising units of formula (VIII):

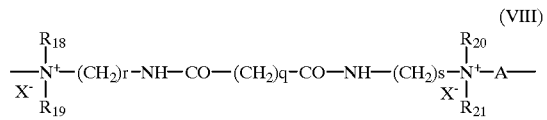 (VIII)

wherein:

$R_{18}$, $R_{19}$, $R_{20}$ and $R_{21}$ independently denote a hydrogen atom or a methyl, ethyl, propyl, β-hydroxyethyl, β-hydroxypropyl or —$CH_2CH_2(OCH_2CH_2)_p$OH radical;

p is equal to 0 or to an integer ranging from 1 to 6 if $R_{18}$, $R_{19}$, $R_{20}$ and $R_{21}$ do not simultaneously denote a hydrogen atom;

r and s independently represent integers ranging from 1 to 6;

q is equal to 0 or to an integer ranging from 1 to 34;

X denotes a halogen atom; and

A denotes a radical of a dihalide or preferably denotes —$CH_2$—$CH_2$—O—$CH_2$—$CH_2$—.

Such compounds are described especially in patent application EP-A-122 324, the disclosure of which is specifically incorporated by reference herein.

Among these there may be mentioned, for example, products "Mirapol A 15", "Mirapol AD1", "Mirapol AZ1" and "Mirapol 175", sold by the Miranol company.

(12) Homopolymers or copolymers derived from acrylic or methacrylic acids

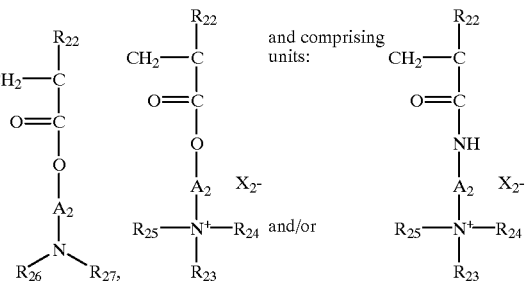

wherein:

the groups $R_{22}$ independently denote H or $CH_3$; groups $A_2$ independently denote a linear or branched alkyl group with 1 to 6 carbon atoms or a hydroxyalkyl group with 1 to 4 carbon atoms;

groups $R_{23}$, $R_{24}$ and $R_{25}$ independently denote an alkyl group with 1 to 18 carbon atoms or a benzyl radical;

groups $R_{26}$ and $R_{27}$ denote a hydrogen atom or an alkyl group with 1 to 6 carbon atoms; and $X_2^-$ denotes an anion, for example methosulphate or halide, such as chloride or bromide.

The comonomer(s) which may be employed in the preparation of the corresponding copolymers belong to the class of acrylamides, methacrylamides, diacetone acrylamides, acrylamides and methacrylamides substituted under nitrogen by lower alkyls, alkyl esters, acrylic or methacrylic acids, vinylpyrrolidone or vinyl esters.

(13) Quaternary vinylpyrrolidone and vinylimidazole polymers such as, for example, the products marketed under the names Luviquat FC 905, FC 550 and FC 370 by the company B.A.S.F.

(14) Polyamines like the Polyquart H sold by Henkel, referred to under the name of "Polyethylene glycol (15) Tallow Polyamine" in the CTFA dictionary.

(15) The crosslinked methacryloyloxyethyltrimethylammonium chloride polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide.

More particularly, it is possible to employ a crosslinked acrylamide/methacryloyloxyethyltrimethylammonium chloride copolymer (20/80 by weight) in the form of dispersion containing 50% by weight of the said copolymer in mineral oil. This dispersion is marketed under the name of "Salcare SC 92" by the Allied Colloids company.

It is also possible to employ a crosslinked methacryloyloxyethyltrimethylammonium chloride homopolymer containing approximately 50% by weight of the homopolymer in mineral oil. This dispersion is marketed under the name of "Salcare SC 95" by the Allied Colloids company.

Other cationic polymers that may be employed within the scope of the invention are polyalkyleneimines, in particular polyethyleneimines, polymers containing vinylpyridine or vinylpyridinium units, condensates of polyamines and of epichlorohydrin, quaternary polyureylenes and chitin derivatives.

According to the invention it is possible to employ more particularly the polymers chosen from Mirapol, the compound of formula (VII) in which $R_{13}$, $R_{14}$, $R_{15}$ and R16 denote the methyl radical, $A^1$ denotes the radical of formula —(CH$_2$)$_3$— and B$_1$ denotes the radical of formula —(CH$_2$)$_6$— and X$^-$ denotes the chloride anion (subsequently called Mexomere PO) and the compound of formula (VII) in which $R_{13}$ and $R_{14}$ denote the ethyl radical, $R_{15}$ and $R_{16}$ denote the methyl radical, $A_1$ and $B_1$ denote the radical of formula —(CH$_2$)$_3$— and X$^-$ denotes the bromide anion (subsequently called Mexomere PAK).

Among all the cationic polymers capable of being employed within the scope of the present invention it is preferred to use quaternary cellulose ether derivatives such as the products sold under the name "JR 400" by the company Union Carbide Corporation, cyclopolymers, in particular the copolymers of dimethyidiallylammonium chloride and of acrylamide which have a molecular weight higher than 500 000, sold under the names "Merquat 550" and "Merquat S" by the Merck company, cationic polysaccharides and more particular the polymer sold under the name "Jaguar C13S" by the Meyhall company and, finally, silicone cationic polymers.

According to the invention the cationic polymer(s) may represent from 0.01 to 10% by weight, preferably from 0.05% to 5% by weight, and still more preferably from 0.1% to 3% by weight, of the total weight of the final composition.

C- SILICONE DERIVATIVE(S)

According to an essential characteristic of the detergent hair compositions in accordance with the invention, these additionally comprise at least one water-soluble or water-dispersible specific silicone derivative.

In what follows, silicone is intended to denote—in agreement with the general understanding—any organosilicon polymers or oligomers of linear or cyclic, branched or crosslinked structure, of variable molecular weight, which are obtained by polymerization and/or polycondensation of suitably functionalized silanes and comprising a repetition of main units in which the silicon atoms are joined together by oxygen atoms ($\equiv$Si—O—Si$\equiv$ siloxane bond), optionally substituted hydrocarbon radicals being joined directly through the intermediacy of a carbon atom to the said silicon atoms.

The most common hydrocarbon radicals are the alkyl radicals, especially $C_1$–$C_{10}$ and in particular methyl, fluoroalkyl radicals, aryl radicals and in particular phenyl, and alkenyl radicals and in particular vinyl; other types of radicals capable of being joined either directly or through the intermediacy of a hydrocarbon radical to the siloxane chain are especially hydrogen, the halogens and in particular chlorine, bromine or fluorine, thiols, alkoxy radicals, polyoxyalkylene radicals (or polyethers) and in particular polyoxyethylene and/or polyoxypropylene, hydroxyl or hydroxyalkyl radicals, substituted or unsubstituted amine groups, amide groups, acyloxy or acyloxyalkyl radicals, hydroxyalkylamino or aminoalkyl radicals, quaternary ammonium groups, amphoteric or betainic groups, anionic groups such as carboxylates, thioglycolates, sulphosuccinates, thiosulphates, phosphates and sulphates, this list not being, of course, limiting in any way (so-called "organomodified" silicones).

According to the present invention the silicone derivative (s) which must be employed are those which include a silicone (or polysiloxane ($\equiv$Si—O—)$_n$) main chain on which there is grafted at least one hydrocarbon group of anionic character, within the said chain and optionally at at least one of its ends.

Within the meaning of the present invention a hydrocarbon group "of anionic character" is intended to mean any hydrocarbon group 2 0 containing at least one anionic unit or at least one unit which can be ionized to an anionic unit. According to an essential characteristic of the present invention the nature and/or the quantity of the said hydrocarbon groups of anionic character which are grafted onto the silicone chain must be chosen so that the corresponding silicone derivative is water-soluble or water-dispersible, after possible neutralization of the groups of anionic character by means of an alkaline agent.

These particular silicone derivatives may be existing commercial products, or else may be obtained by any means known to a person skilled in the art, in particular by reaction between (i) a starting silicone correctly functionalized on one or more of these silicon atoms and (ii) an anionic compound, itself correctly functionalized by a functional group which is capable of reacting with the functional group(s) carried by the said silicone by forming a covalent bond; a classic example of such a reaction is the hydrosilylation reaction between ≡Si—H groups and CH$_2$=CH— vinyl groups, or else the reaction between —SH thiofunctional groups with these same vinyl groups.

According to a particularly preferred embodiment of the present invention the said hydrocarbon group of anionic character includes the result of the radical (homo) polymerization of at least one anionic monomer containing ethylenic unsaturation.

According to another particularly preferred embodiment of the present invention the silicone derivative used includes the result of the radical copolymerization between, on the one hand, at least one anionic monomer exhibiting an ethylenic unsaturation and, on the other hand, a silicone exhibiting in its chain at least one, and preferably several, functional groups capable of reacting with the said ethylenic unsaturation of the said anionic monomer by forming a covalent bond, in particular thiofunctional groups.

According to the present invention the anionic monomers containing ethylenic unsaturation are preferably chosen, alone or as mixtures, from linear or branched, unsaturated carboxylic acids, optionally partially or completely neutralized in the form of a salt, it being possible for this or these carboxylic acids to be more particularly acrylic acid, methacrylic acid, maleic acid, maleic anhydride, itaconic acid, fumaric acid and crotonic acid.

The suitable salts are especially the alkali or alkaline-earth metal and ammonium salts. It will be noted that, similarly, in the final silicone derivative, the hydrocarbon group of anionic character which includes the result of the radical (homo)polymerization of at least one anionic monomer of unsaturated carboxylic acid type may be, after reaction, post-neutralized with a base (sodium hydroxide, aqueous ammonia, etc) in order to bring it into the form of a salt.

Examples of silicone derivatives which are suitable for making use of the present invention, as well as their particular method of preparation, are described especially in patent applications EP-A-0 582,152 and WO 93/23009, the disclosures of which are specifically incorporated by reference herein.

Among the silicone derivatives described in these two documents it is appropriate to retain, as indicated above, only those in the case of which the polysiloxane chain comprises anionic polymeric grafts capable of endowing the final product with its water-soluble or water-dispersible nature.

A class of silicone derivatives which is particularly well suited for making use of the present invention consists of the silicone derivatives comprising the following unit in their structure:

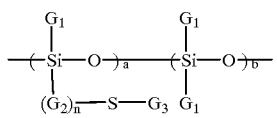

(IX)

wherein
$G_1$ denotes hydrogen or a $C_1$–$C_{10}$ alkyl radical or else a phenyl radical;
$G_2$ denotes a $C_1$–$C_{10}$ alkylene group;
$G_3$ denotes an anionic polymeric residue resulting from the (homo)polymerization of at least one anionic monomer containing ethylenic unsaturation;

n is equal to 0 or 1;
a is an integer preferably ranging from 1 to 50; and
b is an integer preferably ranging from 10 to 350.

The unit of formula (IX) above preferably exhibits at least one, and still more preferably the combination, of the following characteristics:

$G_1$ is a $C_1$–$C_{10}$ alkyl radical, preferably the methyl radical, n is not zero and $G_2$ denotes a $C_1$–$C_3$ divalent radical, preferably a $C_1$–$C_3$ alkylene radical, and more preferably a propylene radical, $G_3$ denotes a polymeric radical resulting from the (homo) polymerization of at least one monomer of the unsaturated carboxylic acid type, preferably acrylic and/or methacrylic acid.

The carboxylate group content in the final polymer preferably ranges from 1 mole of carboxylate per 200 g of polymer to 1 mole of carboxylate per 5000 g of polymer.

The number molecular mass of the silicone polymer preferably ranges from 10,000 to 1,000,000 and still more preferably from 10,000 to 100,000.

Examples of silicone derivatives which are particularly well suited to the carrying out of the present invention are especially those sold by the 3M company under the trade name of "Silicones "Plus" Polymers VS 80". These products correspond to polydimethylsiloxanes (PDMS) onto which are grafted, through the intermediacy of a connecting link of thiopropylene type, mixed polymer units of the poly(meth) acrylic acid type and of the butyl poly(meth)acrylate ester type. These products can be obtained conventionally by radical copolymerization between, on the one hand, a silicone of polydimethylsiloxane type previously functionalized with thiopropyl groups and, on the other hand, a mixture of monomers comprising (meth)acrylic acid and of butyl (meth)acrylate.

The hair compositions in accordance with the invention contain the silicone derivatives defined above in weight contents which may preferably range from 0.05% to 10%, and more preferably from 0.1% to 5% and, still more preferably, from 0.2% to 3%, relative to the total weight of the composition.

The carrier, or support, of the detergent compositions according to the invention is preferably water or a hydroalcoholic solution of a lower alcohol such as ethanol, isopropanol or butanol.

The detergent compositions according to the invention have a final pH which generally ranges from 3 to 10. This pH more preferably ranges from 5.5 to 8. The adjustment of the pH to the desired value may be made conventionally by adding a base (organic or inorganic) into the composition, for example aqueous ammonia or a primary, secondary or tertiary (poly)amine like monoethanolamine, diethanolamine, triethanolamine, isopropanolamine or 1,3-propanediamine, or else by adding an acid, preferably a carboxylic acid such as, for example, citric acid.

The detergent compositions according to the invention may, of course, additionally contain any of the usual adjuvants encountered in the field of shampoos, like, for example, perfumes, preserving agents, sequestrants, thickeners, emollients, foam modifiers, colorants, pearlescent agents, hydrating agents, antidandruff or antiseborrhoeic agents, vitamins, sunscreens and others.

A person skilled in the art will know how to choose this or these optional additional compound(s) and/or their quantities so that the advantageous properties intrinsically attached to the ternary association (washing base+cationic polymer+specific silicone derivative) in accordance with the invention are not, or are substantially not, impaired by the envisaged addition(s).

These compositions may be in the form of more or less thickened liquids, of creams or of gel and are suitable chiefly for the washing, the care and/or the styling of hair. They may also be presented in the form of rinsing lotions.

When the compositions in accordance with the invention are used as conventional shampoos, they are simply applied to wet hair and the foam generated by massaging or rubbing with the hands is subsequently removed, after an optional interval, by rinsing with water, it being possible for the operation to be repeated one or more times.

As indicated above, the compositions in accordance with the invention endow the hair, after rinsing, with a remarkable styling effect which is reflected especially in an ease of styling and of holding the style, as well as a contribution of body and lightness, which are markedly improved.

Concrete examples illustrating the invention will now be given, without any limitation being implied.

EXAMPLE 1

Two shampoo compositions were produced, one in accordance with the invention (composition A) and the other comparative (composition B), differing from each other simply in the nature of the silicone derivative employed:

|  | Composition A | Composition B |
| --- | --- | --- |
| Sodium lauryl ether sulphate ($C_{12}/C_{14}$, 70/30) containing 2.2 moles of ethylene oxide (AS = active substance) | 11.8 g AS | 11.8 g AS |
| Cocoylbetaine | 2.56 g AS | 2.56 g AS |
| Xanthan gum | 1 g | 1 g |
| Cationic polymer (*) | 0.5 g AS | 0.5 g AS |
| Silicone derivative 1 (**) | 0.5 g AS | — |
| Silicone derivative 2 (***) | — | 0.5 g AS |
| Demineralized water | q.s. 100 g | q.s. 100 g |

*Dimethyldiallylammonium chloride/acrylamide (50/50) copolymer sold in aqueous solution under the name of Merquat 550 by the Calgon company.
**Polydimethyl/methylsiloxane containing propyl thio 3 polymethacrylic acid/polyisobutyl methacrylate groups, preneutralized with aqueous ammonia and sold in aqueous solution under the name of VS 80 by the 3M company.
***Polydimethyl/methylsiloxane containing propyl thio 3 polyisobutyl-methacrylate groups sold in a solution of silicone D4 under the name of VS 70 by the 3M company.

Strands of 2.7 g of bleached hair (15.7% of alkaline solubility) 24 cm in length were prewetted and then placed in contact with 1 g of the composition A according to the invention for 10 minutes and then rinsed with water.

Still wet, the strands were then wound onto curlers 2 cm in diameter and 7 cm in length. The strands were then dried for 30 minutes in a helmet hairdrier and then carefully removed from the curlers. Curled dried strands were thus obtained.

The same procedure as above was followed with the comparative composition B.

The length (L) of the curled strands suspended only by their weight was then measured before a graduated panel.

They were then allowed to relax, still suspended, for 4 hours at ambient temperature.

The length of the suspended strands then increased by a certain length (ΔL). The smaller this lengthening ΔL, the better the style holding with time.

Thus, with the composition B, the lengthening was 3.6 cm, whereas it was only 3 cm with the composition A; that is an improvement in the reduction of the lengthening of more than 16%, which reflects well the better style holding obtained by virtue of the shampoo according to the invention.

EXAMPLE 2

Two shampoo compositions were produced, one in accordance with the invention (composition C) and the other comparative (composition D), differing from each other simply in the presence or absence of a silicone derivative in accordance with the invention:

|  | Composition C | Composition D |
| --- | --- | --- |
| Sodium lauryl ether sulphate ($C_{12}/C_{14}$, 70/30) containing 2.2 moles of ethylene oxide (AS = active substance) | 11.8 g AS | 11.8 g AS |
| Cocoylbetaine | 2.56 g AS | 2.56 g AS |
| Cationic polymer (*) | 0.5 g AS | 2.5 g AS |
| Silicone derivative 1 (**) | 2 g AS | — |
| Demineralized water | q.s. 100 g | q.s. 100 g |

*Identical with that in Example 1 (Merquat 550).
**Identical with that in Example 1 (VS 80).

Strands of 2.7 g of bleached hair (15.7% of alkaline solubility) 24 cm in length were prewetted and then placed in contact for a first time with 1 g of the composition C according to the invention for 10 minutes and were then rinsed with water and then placed in contact a second time with 1 g of this same composition C, again for 10 minutes, and were finally rinsed a second time.

Still wet, the strands were then wound onto curlers 2 cm in diameter and 7 cm in length. The strands were then dried for 30 minutes in the helmet hairdrier and then carefully removed from the curlers. Curled dried strands were thus obtained.

The same procedure as above was followed with the comparative composition D of the prior art.

A panel of 10 experts then compared the compressibility of the strands. The easier the manual distortion, the less satisfactory is the style holding effect.

For the ten experts the strand treated with the composition C according to the invention was less liable to distortion than that treated with the comparative composition D, which reflects well the superiority of the styling effect attached to the shampoo according to the invention.

We claim:

1. A detergent hair composition comprising, in a cosmetically acceptable medium, a washing base having detergent power and at least one cationic polymeric conditioning agent, wherein said composition further comprises at least one water-soluble or water-dispersible silicone compound including a silicone main chain onto which at least one hydrocarbon group of anionic nature is grafted.

2. A composition according to claim 1, wherein said washing base includes at least one anionic, amphoteric, nonionic, zwitterionic, or cationic surfactant.

3. A composition according to claim 1, wherein said washing base is present in a weight content ranging from 4% to 30% relative to the total weight of the composition.

4. A composition according to claim 3, wherein said washing base is present in a weight content ranging from 10% to 25% relative to the total weight of the composition.

5. A composition according to claim 4, wherein said washing base is present in a weight content ranging from 12% to 20% relative to the total weight of the composition.

6. A composition according to claim 1, wherein said at least one cationic surfactant is a quaternary cellulose ether polymer, a cyclopolymer, a cationic polysaccharide, or a silicone cationic polymer.

7. A composition according to claim 6, wherein said cyclopolymer is a copolymer of dimethyldiallylammonium chloride and of acrylamide which has a molecular weight higher than 500,000.

8. A composition according to claim 1, wherein said at least one cationic polymer is present in a weight content ranging from 0.01% to 10% relative to the total weight of the composition.

9. A composition according to claim 8, wherein said at least one cationic polymer is present in a weight content ranging from 0.05% to 5% relative to the total weight of the composition.

10. A composition according to claim 9, wherein said at least one cationic polymer is present in a weight content ranging from 0.1% to 3% relative to the total weight of the composition.

11. A composition according to claim 1, wherein said at least one hydrocarbon group of anionic nature includes at least one radical (homo)polymerized anionic monomer containing ethylenic unsaturation.

12. A composition according to claim 1, wherein said silicone compound includes the radical copolymerized compound of
   (i) at least one anionic monomer containing ethylenic unsaturation; and
   (ii) a silicone containing in its chain at least one functional group capable of reacting with the said ethylenic unsaturation of the said anionic monomer by forming a covalent bond.

13. A composition according to claim 12, wherein said at least one functional group carried by the said silicone compound is a thiofunctional group.

14. A composition according to claim 11, wherein said at least one anionic monomer containing ethylenic unsaturation is a linear or branched, unsaturated carboxylic acid, optionally partially or completely neutralized in the form of a salt.

15. A composition according to claim 14, wherein said carboxylic acid, which can be partially or completely neutralized in the form of a salt, is acrylic acid, methacrylic acid, maleic acid, maleic anhydride, itaconic acid, fumaric acid, or crotonic acid.

16. A composition according to claim 1, wherein said silicone compound is a silicone compound comprising the following unit in its structure:

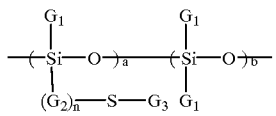

wherein
   $G_1$ independently denotes hydrogen or a $C_1$–$C_{10}$ alkyl radical or a phenyl radical;
   $G_2$ denotes a $C_1$–$C_{10}$ alkylene group;
   $G_3$ denotes an anionic polymeric residue from at least one radical (homo)polymerized anionic monomer containing ethylenic unsaturation;
   n is equal to 0 or 1;
   a is an integer ranging from 1 to 50; and
   b is an integer ranging from 10 to 350.

17. A composition according to claim 16, wherein $G_1$ is said $C_1$–$C_{10}$ alkyl radical.

18. A composition according to claim 17, wherein said $C_1$–$C_{10}$ alkyl radical is a methyl radical.

19. A composition according to claim 16, wherein n is 1 and $G_2$ denotes a $C_1$–$C_3$ alkylene radical.

20. A composition according to claim 19, wherein said alkylene radical is a propylene radical.

21. A composition according to claim 16, wherein $G_3$ denotes a polymeric radical of the (homo)polymerized at least one unsaturated carboxylic acid anionic monomer.

22. A composition according to claim 21, wherein said unsaturated carboxylic acid anionic monomer is selected from acrylic acid and methacrylic acid.

23. A composition according to claim 21, wherein said silicone compound has a carboxylate group content ranging from 1 mole of carboxylate per 200 g of silicone compound to 1 mole of carboxylate per 5000 g of silicone compound.

24. A composition according to claim 1, wherein said silicone compound has a number molecular mass ranging approximately from 10,000 to 1,000,000.

25. A composition according to claim 24, wherein said silicone compound has a number molecular mass ranging approximately from 10,000 and 100,000.

26. A composition according to claim 1, wherein said silicone compound is a polydimethyl/methylsiloxane comprising propyl thio 3 polymethacrylic acid/polyisobutyl methacrylate groups.

27. A composition according to claim 1, wherein said silicone compound is present in a weight content ranging from 0.05% to 10%, relative to the total weight of the composition.

28. A composition according to claim 27, wherein said silicone compound is present in a weight content ranging from 0.1% to 5%, relative to the total weight of the composition.

29. A composition according to claim 28, wherein said silicone compound is present in a weight content ranging from 0.2% to 3%, relative to the total weight of the composition.

30. A composition according to claim 1, wherein said composition has a pH ranging from 3 to 10.

31. A composition according to claim 30, wherein said composition has a pH ranging from 5.5 to 8.

32. A method of cleaning and/or caring and/or conditioning and/or styling hair comprising the step of applying to said hair an effective amount of a composition according to claim 1.

33. A method of improving the styling effect of a detergent hair composition containing at least one cationic polymer by including in said hair composition at least one silicone compound according to claim 1.

34. A composition according to claim 2, wherein said washing base is present in an amount sufficient to provide to said hair composition satisfactory foamability and detergency.

35. A composition according to claim 2, wherein said at least one surfactant is an alkylpolyglycoside.

36. A composition according to claim 1, wherein said at least one cationic polymer is a polymer containing units comprising primary, secondary, tertiary, and quaternary amine groups either as part of the main polymer chain or carried by a side substituent bonded directly to the main polymer chain.

37. A composition according to claim 1, wherein said at least one cationic polymer has a molecular mass ranging approximately from 500 to 5000.

38. A composition according to claim 1, wherein said at least one cationic polymer has a molecular mass ranging approximately from $10^3$ to $3 \times 10^6$.

39. A composition according to claim 1, wherein said at least one cationic polymer is a quaternized protein, a protein hydrolysate, a quaternized polysiloxane, a quaternary polyamine, a quaternary polyaminoamide or a polyammonium polymer.

40. A composition according to claim 6, wherein said at least one cationic polymer is a quaternary cellulose ether polymer.

41. A composition according to claim 1, wherein said composition additionally comprises at least one adjuvant.

42. A composition according to claim 1, wherein said composition is in the form of a thickened liquid, a cream, a gel, or a rinsing lotion.

* * * * *

UNITED STATES PATENT AND TRADEMARK OFFICE
CERTIFICATE OF CORRECTION

PATENT NO. : 6,022,836
DATED : February 8, 2000
INVENTOR(S) : DUBIEF ET AL.

It is certified that error appears in the above-identified patent and that said Letters Patent is hereby corrected as shown below:

Title page, item [22],
   Filing Date: July 5, 1996

Signed and Sealed this

Twenty-eighth Day of November, 2000

Attest:

Q. TODD DICKINSON

Attesting Officer

Director of Patents and Trademarks